US008956517B2

(12) United States Patent
Sundara et al.

(10) Patent No.: US 8,956,517 B2
(45) Date of Patent: Feb. 17, 2015

(54) NANOCOMPOSITE BASED BIOSENSORS AND RELATED METHODS

(75) Inventors: Ramaprabhu Sundara, Chennai (IN); Tessy Theres Baby, Chennai (IN)

(73) Assignee: Indian Institute of Technology Madras, Chennai, Tamil Nadu (IN)

( * ) Notice: Subject to any disclaimer, the term of this patent is extended or adjusted under 35 U.S.C. 154(b) by 376 days.

(21) Appl. No.: 12/827,613

(22) Filed: Jun. 30, 2010

(65) Prior Publication Data
US 2012/0000795 A1 Jan. 5, 2012

(51) Int. Cl.
  G01N 27/26 (2006.01)
  G01N 27/327 (2006.01)
  B82Y 25/00 (2011.01)
  H01F 1/00 (2006.01)

(52) U.S. Cl.
  CPC ........... G01N 27/3278 (2013.01); B82Y 25/00 (2013.01); H01F 1/0063 (2013.01); H01F 1/0054 (2013.01); Y10S 977/747 (2013.01); Y10S 977/92 (2013.01); Y10S 977/957 (2013.01)
  USPC ...... 204/403.01; 205/792; 977/747; 977/920; 977/957

(58) Field of Classification Search
  USPC ............ 204/403.01–403.15; 205/777.5, 778, 205/792; 977/747, 920, 957
  See application file for complete search history.

(56) References Cited

U.S. PATENT DOCUMENTS

2009/0280242 A1* 11/2009 Winarski ...................... 427/130

OTHER PUBLICATIONS

S. Qu, J. Wang, J. Kong. P. Yang, G. Chen, Magnetic loading of carbon nanotube/nano-Fe3O4 composite for electrochemical sensing, Talanta 71 (2007) 1096-1102.*
M. Yang, J. Jiang, Y. Yang, X. Chen, G. Shen, R. Yu, Carbon nanotube/cobalt hexacyanoferrate nanoparticle-biopolymer system for the fabrication of biosensors, Biosensors and Bioelectronics 21, 1791-1797 (2005).*
Sébastien Vaucher, John Fielden, Mei Li, Erik Dujardin, and Stephen Mann Molecule-Based Magnetic Nanoparticles: Synthesis of Cobalt Hexacyanoferrate, Cobalt Pentacyanonitrosylferrate, and Chromium Hexacyanochromate Coordination Polymers in Water-in-Oil Microemulsions, Nano Letters 2 (3), 225-229 (2002).*
Banks, C.E. et al., "Exploring the Electocatalytic Sites of Carbon Nanotubes for NADH Detection: An Edge Plane Pyrolytic Graphite Electrode Study," Analyst,130, 2005, pp. 1232-1239.
Chen, R.J. et al., "Noncovalent Sidewall Functionalization of Single-Walled Carbon Nanotubes for Protein Immobilization," J. Am. Chem. Soc., 123, 2001, pp. 3838-3839.
Chiang, I.W. et al., "Purification and Characterization of Single-Wall Carbon Nanotubes," J. Phys. Chem. B, vol. 105, 2001, pp. 1157-1161.

(Continued)

Primary Examiner — Luan Van
Assistant Examiner — Maris R Kessel
(74) Attorney, Agent, or Firm — Foley & Lardner LLP

(57) ABSTRACT

Disclosed are nanocomposite-based biosensors. The biosensors include an electrode, a nanocomposite over the surface of the electrode, the nanocomposite comprising a population of carbon nanotubes and a population of magnetic nanoparticles dispersed in the population of carbon nanotubes, wherein the magnetic nanoparticles comprise a ferromagnetic metal or compound thereof, and one or more biomolecules over the surface of the electrode, wherein the biomolecules are capable of undergoing a redox reaction with a target molecule. Also disclosed are nanocomposites, modified electrodes, kits, and methods for using the biosensors.

19 Claims, 14 Drawing Sheets

(56) References Cited

OTHER PUBLICATIONS

Chu, X. et al., "Amperometric Glucose Biosensor Based on Electrodeposition of Platinum Nanoparticles onto Covalently Immobilized Carbon Nanotube Electrode," Talanta, 71, 2007, pp. 2040-2047.
Daniel, S. et al., "A Review of DNA Functionalized/Grafted Carbon Nanotubes and their Characterization," Sensors and Actuators B, 122, 2007, pp. 672-682.
Geng, H.Z. et al., "Opening and Closing of Single-Wall Carbon Nanotubes," Chem. Phys. Lett., 399, 2004, pp. 109-113.
Guo, M. et al., "Electrochemical Characteristics of the Immobilization of Calf Thymus DNA Molecules on Multi-Walled Carbon Nanotubes," Bioelectrochemistry, 62, 2004, pp. 29-35.
Heitmann, J. et al., "Silicon Nanocrystals: Size Matters," Adv. Mater., vol. 17, No. 7, Apr. 4, 2005, pp. 795-803.
Jiang, K. et al., "Protein Immobilization on Carbon Nanotubes via a Two-Step Process of Diimide-Activated Amidation," J. Mater. Chem., 14, 2004, pp. 37-39.
Josephson, L. et al., "Magentic Nanosensors for the Detection of Oligonucleotide Sequences," Angew. Chem. Int. Ed., vol. 40, 2001, pp. 3204-3206.
Liu, Y. et al., "Amperometric Glucose Biosensing of Gold Nanoparticles and Carbon Nanotube Multilayer Membranes," Electroanalysis, vol. 19, No. 9, 2007, pp. 986-992.
Liu, Z. et al., "A Phenol Biosensor Based on Immobilizing Tyrosinase to Modified Core-Shell Magnetic Nanoparticles Supported at a Carbon Paste Electrode," Anal. Chim. Acta, 533, 2005, pp. 3-9.
Lu, Z. et al., "Facile Synthesis of $Fe_3O_4/SiO_2$ Composite Nanoparticles from Primary Silica Particles," Colloids and Surfaces A, 317, 2008, pp. 450-456.
Male, K.B. et al., "Electrochemical Detection of Carbohydrates Using Copper Nanoparticles and Carbon Nanotubes," Anal. Chim. Acta, 516, 2004, pp. 35-41.
Qiu, J. et al., "Ferrocene-modified $Fe_3O_4@SiO_2$ Magnetic Nanoparticles as Building Blocks for Construction of Reagentless Enzyme-Based Biosensors," Electrochemistry Communications, 9, 2007, pp. 2734-2738.
See, K.H. et al., "A Reactive Core-Shell Nanoparticle Approach to Prepare Hybrid Nanocomposites: Effects of Processing Variables," Nanotechnology, 16, 2005, pp. 1950-1959.
Tahir, Z.M. et al., "Polyaniline Synthesis and its Biosensor Application," Biosensors and Bioelectronics, 20, 2005, pp. 1690-1695.
Theres Baby, T.T. et al., "$SiO_2$ coated $Fe_3O_4$ Magnetic Nanoparticle Dispersed Multiwalled Carbon Nanotubes Based Amperometric Glucose Biosensor," Talanta, 80, 2010, pp. 2016-2022.
Wellman, A.D. et al., "Magnetically-Assisted Transport Evanescent Field Fluoroimmunoassay," Anal. Chem., 78, 2006, pp. 4450-4456.
Zhang, S. et al., "Covalent Attachment of Glucose Oxidase to an Au Electrode Modified with Gold Nanoparticles for use as Glucose Biosensor," Bioelectrochemistry, 67, 2005, pp. 15-22.
Zhao, X. et al., "Competitive Immunoassay for Microliter Protein Samples with Magentic Beads and Near-Infrared Fluorescence Detection," Anal. Chem., 76, 2004, pp. 1871-1876.
Chen, C.S., et al., "Zinc oxide nanoparticle decorated multi-walled carbon nanotubes and their optical properties," Acta Materialia, vol. 54, Issue 20, pp. 5401-5407, 2006.
Chen, F.H., et al., "The grafting and release behavior of doxorubicin from Fe3O4@SiO2 core013shell structure nanoparticles via an acid cleaving amide bond: the potential for magnetic targeting drug delivery ," Nanotechnology, vol. 19, No. 16, 9 pages, 2008.
Correa-Duarte, M.A., et al., "Control of Packing Order of Self-Assembled Monolayers of Magnetite Nanoparticles with and without SiO2 Coating by Microwave Irradiation," Langmuir, vol. 14, pp. 6430-6435, 1998.
Dagan G., et al. ,"Passivation of Permalloy .2. Thin-Films Insitu Characterization of the Oxide Layer by Photoelectrochemical and Impedance Measurements," Journal of the Electrochemical Society, vol. 139, Issue 7, p. 1855-1861, 1992.
Lan, Q., et al., "Synthesis of bilayer oleic acid-coated Fe3O4 nanoparticles and their application in pH-responsive Pickering emulsions," Journal of Colloid and Interface Science, vol. 310, Issue 1, pp. 260-269, 2007.
Tie, S.L., et al., "Monodisperse Fe3O4/Fe@SiO2 core/shell nanoparticles with enhanced magnetic property ," Colloids and Surfaces A: Physicochemical and Engineering Aspects, vol. 293, Issue 13, pp. 278-285, 2007.

\* cited by examiner

NANOCOMPOSITE BASED BIOSENSORS AND RELATED METHODS

BACKGROUND

The following description is provided to assist the understanding of the reader. None of the information provided or references cited is admitted to be prior art.

A biosensor is a sensing device formed from a specific biological element sensitive to a particular analyte and a transducer element, e.g., an electrode, that transforms the signal resulting from the interaction of the analyte with the biological element into another signal that can be measured and quantified. Biosensor electrodes may be modified with nanomaterials. The nanomaterials may increase the surface area of the electrode, retain the bioactivity of the biological element, and facilitate electron transfer between the biological element and the electrode.

Glucose biosensors find use in a variety of areas such as clinical diagnostics, biotechnology and the food industry. Many glucose biosensors are based on the reaction shown in Scheme I, in which the enzyme, glucose oxidase (GOD), catalyzes the oxidation of glucose to gluconolactone and $H_2O_2$ with the assistance of oxygen.

Scheme I

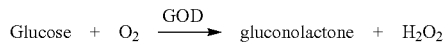

The concentration of glucose can be determined via electrochemical detection of the enzymatically liberated $H_2O_2$. However, many conventional glucose biosensors, including biosensors having electrodes modified with nanomaterials, exhibit less than desired characteristics in one or more of sensitivity, response times, and range of detection, limiting their usefulness in the applications noted above.

SUMMARY

Disclosed herein are nanocomposite-based biosensors and components thereof, including nanocomposites and modified electrodes. Also provided are kits for making and using the biosensors and methods for using the biosensors to determine the concentration of a target molecule in a sample.

In one aspect, a biosensor is provided, the biosensor includes: an electrode; a nanocomposite over the surface of the electrode, the nanocomposite includes a population of carbon nanotubes and a population of magnetic nanoparticles dispersed in the population of carbon nanotubes, where the magnetic nanoparticles include a ferromagnetic metal or compound thereof; and one or more biomolecules over the surface of the electrode, where the biomolecules are capable of undergoing a redox reaction with a target molecule. In some embodiments, the magnetic nanoparticles include iron, nickel, cobalt, or a compound of iron, nickel, or cobalt. In some embodiments, the magnetic nanoparticles include iron or a compound thereof. In some embodiments, the magnetic nanoparticles include iron oxide. In some embodiments, the magnetic nanoparticles include $Fe_3O_4$.

In one embodiment, the magnetic nanoparticles include core-shell magnetic nanoparticles, where the core includes the ferromagnetic metal or compound thereof. In some embodiments, the shell includes silicon dioxide.

In some embodiments, the magnetic nanoparticles have an average diameter of about 10 nm to about 30 nm.

In one embodiment, the carbon nanotubes include multi-walled carbon nanotubes. In some embodiments, the carbon nanotubes have an average outer diameter of about 30 nm to about 50 nm. In some embodiments, the surface of the carbon nanotubes include one or more functional groups. In some embodiments, the functional groups include carboxylic acid groups.

In one embodiment, the biomolecules include one or more enzymes. In some embodiments, the biomolecules include glucose oxidase and the target molecule includes glucose. In some embodiments, the biosensor exhibits a detection limit for glucose of about 800 nM or less. In some embodiments, the biosensor exhibits a linear response for glucose from about 1 µM to about 30 mM.

In one embodiment, the magnetic nanoparticles include core-shell magnetic nanoparticles and the core includes $Fe_3O_4$ and the shell includes silicon dioxide; the carbon nanotubes include multiwalled carbon nanotubes; and the biomolecules include glucose oxidase and the target molecule includes glucose.

In one aspect, a nanocomposite is provided, the nanocomposite including a population of carbon nanotubes; and a population of magnetic nanoparticles dispersed in the population of carbon nanotubes, where the magnetic nanoparticles include core-shell magnetic nanoparticles, and further where the core includes a ferromagnetic metal or a compound thereof. In some embodiments, the shell includes silicon dioxide. In some embodiments, the magnetic nanoparticles include iron, nickel, cobalt, or a compound of iron, nickel, or cobalt. In some embodiments, the magnetic nanoparticles include iron or a compound thereof. In some embodiments, the magnetic nanoparticles include iron oxide. In some embodiments, the magnetic nanoparticles include $Fe_3O_4$. In some embodiments, the magnetic nanoparticles have an average diameter of about 10 nm to about 30 nm.

In one embodiment, the carbon nanotubes include multi-walled carbon nanotubes. In some embodiments, the carbon nanotubes have an average outer diameter of about 30 nm to about 50 nm. In some embodiments, the surface of the carbon nanotubes include one or more functional groups. In some embodiments, the functional groups include carboxylic acid groups.

In one embodiment of the nanocomposite, the core includes $Fe_3O_4$ and the shell includes silicon dioxide, and the carbon nanotubes include multiwalled carbon nanotubes.

In one aspect, a modified electrode is provided, the modified electrode including an electrode and a nanocomposite over the surface of the electrode, where the nanocomposite includes a population of carbon nanotubes and a population of magnetic nanoparticles dispersed in the population of carbon nanotubes, where the magnetic nanoparticles include core-shell magnetic nanoparticles, and further where the core includes a ferromagnetic metal or a compound thereof. In some embodiments, the electrode is a glassy carbon electrode. In some embodiments, the core includes $Fe_3O_4$ and the shell includes silicon dioxide, and the carbon nanotubes include multiwalled carbon nanotubes.

In one aspect, a method for determining a concentration of a target molecule in a sample is provided, the method including exposing the sample to a biosensor, the biosensor including an electrode; a nanocomposite over the surface of the electrode, the nanocomposite including a population of carbon nanotubes and a population of magnetic nanoparticles dispersed in the population of carbon nanotubes, where the magnetic nanoparticles include a ferromagnetic metal or compound thereof; and one or more biomolecules over the surface of the electrode, where the biomolecules are capable of undergoing a redox reaction with a target molecule, and detecting a signal from the biosensor, where the signal is correlated to the concentration of the target molecule in the sample. In some embodiments, the magnetic nanoparticles include core-shell magnetic nanoparticles and the core includes $Fe_3O_4$ and the shell includes silicon dioxide, and the carbon nanotubes include multiwalled carbon nanotubes. In some embodiments, the biomolecules include glucose oxidase and the target molecule includes glucose. In some embodiments, the sample is a food product.

In one aspect, a kit is provided, the kit including an electrode; a nanocomposite, the nanocomposite including a population of carbon nanotubes and a population of magnetic nanoparticles dispersed in the population of carbon nanotubes, where the magnetic nanoparticles include a ferromagnetic metal or compound thereof; one or more biomolecules, where the biomolecules are capable of undergoing a redox reaction with a target molecule; and instrumentation for detecting a signal from the electrode. In some embodiments, the magnetic nanoparticles include core-shell magnetic nanoparticles and the core includes $Fe_3O_4$ and the shell includes silicon dioxide, and the carbon nanotubes include multiwalled carbon nanotubes. In some embodiments, the biomolecules include glucose oxidase and the target molecule includes glucose.

The foregoing summary is illustrative only and is not intended to be in any way limiting. In addition to the illustrative aspects, embodiments, and features described above, further aspects, embodiments, and features will become apparent by reference to the following drawings and the detailed description.

DETAILED DESCRIPTION

Figure 1:
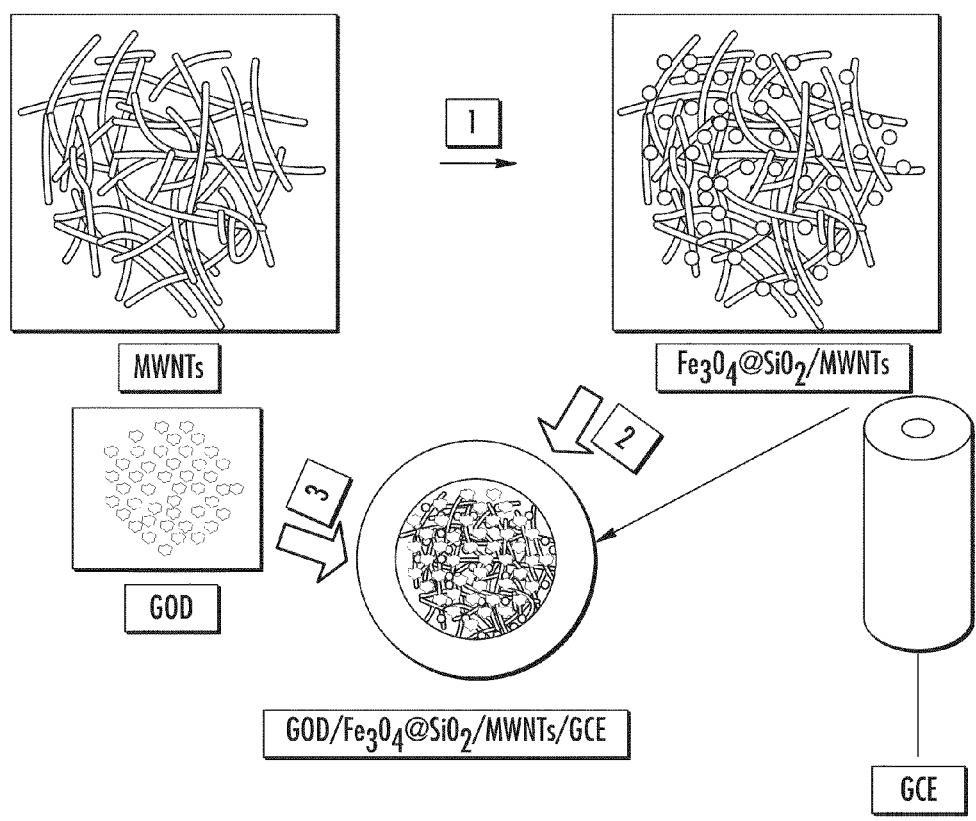
FIG. 1 is a schematic of an illustrative nanocomposite-based biosensor including a glassy carbon electrode (GCE) that has been modified with a nanocomposite of multi-walled carbon nanotubes (MWNTs) and magnetic core-shell nanoparticles having $Fe_3O_4$ cores and $SiO_2$ shells ($Fe_3O_4@SiO_2$) and glucose oxidase (GOD).

In the following detailed description, reference is made to the accompanying figures which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the spirit or scope of the subject matter presented here.

As used herein, unless otherwise stated, the singular forms "a," "an," and "the" include plural reference. Thus, for example, a reference to "a nanoparticle" includes a plurality of nanoparticles, and a reference to "a biomolecule" is a reference to one or more biomolecules.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Disclosed herein are nanocomposite-based biosensors and components thereof, including nanocomposites and modified electrodes. Also provided are kits for making and using the biosensors and methods for using the biosensors to determine the concentration of a target molecule in a sample.

One type of biosensor is a glucose biosensor. Such biosensors are used in a variety of areas such as clinical diagnostics, biotechnology and the food industry. The most useful glucose biosensors are highly sensitive, exhibit fast response times, and exhibit a linear response over a large concentration range, even up to high concentrations of glucose. However, conventional glucose biosensors have problems in achieving these characteristics simultaneously. Some conventional glucose biosensors may be sensitive to low concentrations of glucose, but can only be used over narrow concentration ranges and are not accurate at higher concentrations of glucose. Others may be accurate at higher concentrations of glucose but are not very sensitive. The present technology provides a glucose sensor that is a significant improvement over conventional biosensors as it exhibits surprisingly and unexpectedly high sensitivity, fast response times, and/or linear responses over broad concentration ranges, even up to high concentrations of glucose.

Biosensors

In one aspect, the present disclosure provides a nanocomposite-based biosensor including: an electrode; a nanocomposite over at least a portion of the surface of the electrode; and one or more biomolecules over at least a portion of the surface of the electrode. The nanocomposite includes a population of carbon nanotubes and a population of magnetic nanoparticles dispersed in the population of carbon nanotubes, where the magnetic nanoparticles include a ferromagnetic metal or compound thereof. The biomolecules include biomolecules that are capable of undergoing a redox reaction with a target molecule. Each of these components of the biosensors is further described below.

Nanocomposites

The present disclosure provides nanocomposites which are used for forming the disclosed biosensors. The nanocomposites include a population of carbon nanotubes and a population of magnetic nanoparticles dispersed in the population of carbon nanotubes, where the magnetic nanoparticles include a ferromagnetic metal or compound of a ferromagnetic metal. By "ferromagnetic metal," it is meant a metal that is capable of retaining magnetization in the absence of an externally applied magnetic field. A variety of ferromagnetic metals may be used. In some embodiments, the magnetic nanoparticles include iron, nickel, cobalt, or a compound of iron, nickel, or cobalt. In some embodiments, the magnetic nanoparticles include iron oxide. In some embodiments, the magnetic nanoparticles include the iron oxide, $Fe_3O_4$, meghemite ($\gamma$-$Fe_2O_3$), a mixture of magnetite ($Fe_3O_4$) and meghemite ($\gamma$-$Fe_2O_3$), cobalt, cobalt oxide, nickel, nickel oxide, cobalt-iron oxide ($CoFe_2O_4$), and other magnetic nanoparticles. The disclosed magnetic nanoparticles (or population thereof) may exhibit ferromagnetism, by which it is meant that the magnetic nanoparticles (or population thereof) exhibit spontaneous magnetization, i.e., a net magnetic moment, even in the absence of magnetic field. By paramagnetism it is meant exhibiting magnetism only in the presence of an externally applied magnetic field. The magnetic susceptibility is positive for paramagnetic materials. The disclosed magnetic nanoparticles (or population thereof) may also exhibit superparamagnetism, by which it is meant that the magnetic nanoparticles (or population thereof) can exhibit an external magnetic field is able to magnetize the nanoparticles. Superparamagetism can be exhibited in small ferromagnetic and ferromagnetic materials. This type of material's magnetic susceptibility is larger than that of paramagnetic materials. In some embodiments, the magnetic nanoparticles do not include copper, gold, or platinum nanoparticles.

In some embodiments, the magnetic nanoparticles include core-shell magnetic nanoparticles, where the core includes any of the disclosed ferromagnetic metals or compounds thereof. The shell of the core-shell magnetic nanoparticle includes a material that differs in composition from the material of the core of the core-shell magnetic nanoparticle. A variety of materials may be used for the shell. In some embodiments, the shell includes silicon dioxide, FePt/$MFe_2O_4$ (M=Fe, Co), Au@Pd, Zn/ZnO, Au/$Fe_2O_3$, Au/MnZn, Au, or Pt. The shell material covers the core, although it is to be understood that the shell material need not completely cover the core for the magnetic nanoparticle to be considered a core-shell magnetic nanoparticle.

The dimensions and shapes of the magnetic nanoparticles may vary. The term "nanoparticle" includes particles having at least one dimension ranging from about 1 nm to about 100 nm. This includes particles having at least one dimension ranging from about 2 nm to about 80 nm, from about 5 nm to about 70 nm, from about 10 nm to about 50 nm, or from about 10 nm to about 30 nm. However, other ranges are possible. The term "nanoparticles" includes spherical particles having an aspect ratio of about 1. However, other non-spherical shapes are possible.

It is to be understood that a nanocomposite composition may include magnetic nanoparticles having a range of compositions, dimensions, and shapes within the nanocomposite.

The disclosed nanocomposites also include a population of carbon nanotubes. The term "nanotube" includes tubular, elongated particles having an outside diameter ranging from about 1 nm to about 100 nm. This includes diameters ranging from about 2 nm to about 80 nm, from about 5 nm to about 70 nm, from about 10 nm to about 50 nm, or from about 30 nm to about 50 nm. However, other ranges are possible. The term "nanotube" also includes tubular, elongated particles having a length ranging from 1 μm to 20 cm The carbon nanotubes may include single walled carbon nanotubes (SWNT) or multi-walled carbon nanotubes (MWNT). The surface of the carbon nanotubes may be functionalized with one or more functional groups. These functional groups may be capable of forming covalent bonds with any of the biomolecules disclosed herein. A variety of functional groups are possible. In some embodiments, the functional groups include COOH, OH, NH, $NH_2$, F, COX, and SH, and other functional groups, where X is halogen. Any material attaching to the surface of CNT is a functional group. The functional groups may be identified using FTIR. In MWNTs, each of the carbon shells is closed by various functional groups, such as, but not limited to, —COOH, —OH, OH, NH, and =CO groups. For example, by way of illustration only, FTIR peaks corresponding to C—C bond, $CH_3$ vibration and $CH_2$ vibration also in MWNTs are observed; in $Fe_3O_4$/MWNTs there is a peak around 568 $cm^{-1}$ which corresponds to Fe—O—Fe interaction; and in $Fe_3O_4$@$SiO_2$/MWNTs there is a peak around 1080 $cm^{-1}$ which corresponds to the Si—O—Si interaction.

The disclosed nanocomposites may include other components such as solvents and polymers. The nanocomposites may include a variety of organic solvents. In some embodiments, the nanocomposite includes a sulfonated tetrafluorethylene based fluoropolymer-copolymer. A possible sulfonated tetrafluorethylene based fluoropolymer-copolymer is Nafion, polydiallyldimethylammonium chloride (PDDA), polypyrrole, polydimethylsiloxane, poly(1,2-diaminobenzene), poly(1,3-diaminobenzene/resorcinol), poly(o-phenylenediamine), and cellulose acetate. Such polymers are capable of facilitating the dispersion the magnetic nanoparticles and carbon nanotubes in solution. Other polymers having a similar capability may be used.

A variety of known methods can be used for forming the disclosed magnetic nanoparticles, core-shell magnetic nanoparticles, and carbon nanotubes. Illustrative methods are further described in the Examples below.

Biomolecules

The disclosed biosensors also include one or more biomolecules over at least a portion of the surface of the electrode of the biosensor, where the biomolecules are capable of undergoing a redox reaction with a target molecule. By "redox reaction," it is meant an oxidation-reduction reaction involving the transfer of electrons between the biomolecule and the target molecule. A variety of biomolecules sensitive to a variety of target molecules may be used. Combinations of different biomolecules are also possible. In some embodiments, the biomolecules include enzymes. In some embodiments, the biomolecules include glucose oxidase (GOD) and the target molecule includes glucose; or the biomolecule includes cholesterol oxidase and the target molecule is cholesterol, or the biomolecule includes DNA and the target molecule is dopamine, or the biomolecule includes a cancer drug and the target molecule is a cancer cell. The biomolecules may be, covalently bound, ionically bound, or adsorbed onto the magnetic nanoparticles, the carbon nanotubes, or both, of the nanocomposite.

Electrodes

The disclosed biosensors also include an electrode. A variety of electrodes may be used. In some embodiments, the electrode is a glassy carbon, pyrolytic carbon, gold, silver, platinum, or mercury electrode. As noted above, the surface of the electrode is modified with any of the nanocomposites disclosed herein. Thus, the present disclosure also provides such modified electrodes for use in the disclosed biosensors. The orientation of the carbon nanotubes in the nanocomposite with respect to the surface of the electrode may vary. As shown in FIG. 1, in some embodiments, the carbon nanotubes form an interconnected, mesh-like network of carbon nanotubes over the surface of the electrode. In such a network, the carbon nanotubes may adopt a parallel planar orientation with respect to the electrode, although it is to be understood that the carbon nanotubes need not be perfectly parallel to the surface of the electrode. The carbon nanotubes of the nanocomposite may contact the surface of the electrode, although not all the carbon nanotubes may be in contact with the surface. As also shown in FIG. 1, in some embodiments, the magnetic nanoparticles are dispersed throughout the network of carbon nanotubes. The magnetic nanoparticles can be in contact with one or more carbon nanotubes, although not all of the magnetic nanoparticles may be in contact with carbon nanotubes. Without being bound by theory, it is believed that the carbon nanotubes are held to the electrode via weak vander Waal's interactions or via ionic interactions.

Similarly, the surface of the electrode may be further modified with any of the biomolecules disclosed herein. In some embodiments, the biomolecules form at least a partial layer over the nanocomposite. In some such embodiments, the biomolecules nearly fully cover the nanocomposite. However, it is to be understood that even in such embodiments, one or more biomolecules may become incorporated into the nanocomposite itself so that the biomolecules may not form a perfectly distinct, separate layer over the nanocomposite. As noted above, the biomolecules may be, but need not be, covalently bound to the magnetic nanoparticles, the carbon nanotubes, or both, of the nanocomposite.

The surface of the electrode may be further modified. In some embodiments, the electrode further includes a layer of a sulfonated tetrafluorethylene based fluoropolymer-copolymer, such as Nafion, over the surface of the electrode. This polymer layer may be formed over any nanocomposite and biomolecule layer that has previously been provided over the surface of the electrode.

A variety of known methods can be used for modifying the surface of the disclosed electrodes with the disclosed nanocomposites and biomolecules. Illustrative methods are further described in the Examples below. For example, a solution of any of the disclosed nanocomposites and a solution of any of the disclosed biomolecules may be film-cast onto the surface of the electrode. The concentration of the nanocomposite and the concentration of the biomolecules in the respective solutions may vary. Thus, electrodes may be loaded with varying amounts of nanocomposite and biomolecules by adjusting the concentration of the respective solutions and the parameters of the film-casting technique.

The disclosed biosensors can include a variety of additional components. By way of example, the biosensor may include instrumentation for detecting a signal from the electrode. Such instrumentation is known may include a counter electrode, a reference electrode, a device for measuring current or voltage from the electrodes, and a device for displaying the current or voltage from the electrodes.

Methods

The disclosed biosensors may be used in a variety of applications. Thus, in another aspect, the present disclosure provides a method for determining a concentration of a target molecule in a sample. In one embodiment of such a method, the method includes exposing a sample to any of the disclosed biosensors and detecting a signal from the biosensor, where the signal is correlated to the concentration of the target molecule in the sample. As described above, the disclosed biosensors include an electrode that has been modified with a nanocomposite and one or more biomolecules capable of undergoing a redox reaction with a target molecule. Electrons transferred during a redox reaction between the biomolecules and target molecules will be detected by the electrode of the biosensor. The disclosed nanocomposites, which include magnetic nanoparticles and carbon nanotubes, have excellent electrical conductivity, thereby improving the transfer of electrons between the active redox center of the biomolecule and the electrode. This fast transfer further accelerates the regeneration of the biomolecule for redox reactions with additional target molecules. Thus, the disclosed biosensors are highly sensitive, exhibit fast response times, and are useable over large concentration ranges of target molecules. In fact, as further described in the Examples below, it has been found that the disclosed biosensors are surprisingly and unexpectedly superior to conventional biosensors. In particular, the disclosed sensors exhibit lower detection limits, faster response times, and/or linear responses over greater concentration ranges, even up to high concentrations of target molecules, than conventional biosensors.

The disclosed methods may be used to determine the concentration of a variety of target molecules in a variety of samples, depending upon the biomolecules used in the biosensor. One possible biomolecule/target molecule combination is glucose oxidase/glucose. Biosensors including glucose oxidase as the biomolecule may be used to determine the concentration of glucose in a variety of samples, food products. Such biosensors may also be used to determine the concentration of glucose in a biological sample, such as blood samples. In some embodiments, the biomolecules include glucose oxidase (GOD) and the target molecule includes glucose; or the biomolecule includes cholesterol oxidase and the target molecule is cholesterol, or the biomolecule includes DNA and the target molecule is dopamine, or the biomolecule includes a cancer drug and the target molecule is a cancer cell.

Kits

For the convenience of the user, the components of the biosensor may be provided in a kit including all the equipment for using the biosensor to perform any of the disclosed methods. Thus, in another aspect, the present disclosure provides a kit for determining the concentration of a target molecule in a sample, where the kit includes an electrode, any of the disclosed nanocomposites, any of the disclosed biomolecules, and instrumentation for detecting a signal from the electrode. Instructions may be provided for assembling the components of the kit to form the biosensor and for using the biosensor.

The present technology, thus generally described, will be understood more readily by reference to the following examples, which are provided by way of illustration and are not intended to be limiting.

EXAMPLES

The present disclosure is further illustrated by the following examples, which should not be construed as limiting in any way.

Nanocomposite and Nanocomposite-Based Biosensor

The term "$Fe_3O_4@SiO_2$" refers to core-shell magnetic particles in which the core includes $Fe_3O_4$ and the shell includes $SiO_2$.

Materials

Glucose oxidase (GOD, from *Aspergillus niger*), tetraethoxysilane (TEOS) were purchased from Sigma. 0.1 M phosphate buffer solution (PBS, pH 7) was prepared using potassium phosphate dibasic anhydrous and potassium dihydrogen orthophosphate. Ferric chloride ($FeCl_3 \cdot 6H_2O$), ferrous sulphate ($FeSO_4 \cdot 7H_2O$), ethanol and ammonium hydroxide (25%) were of analytical grade and deionised (dI) water was used throughout.

Example 1A

Preparation of Nanocomposite

Carbon nanotubes were synthesized by catalytic chemical vapour deposition over an alloy hydride catalyst. Rare earth based $AB_3$ alloy hydride was made by arc melting followed by several cycles of hydrogen absorption/desorption process. The catalyst was kept inside a furnace and acetylene (carbon precursor) was introduced at a temperature range 650-750° C., in an inert atmosphere. Pyrolysis of acetylene took place at that temperature and MWNTs began to grow. The as-grown MWNTs were purified before using. The amorphous carbon could be removed by heating the as-grown sample in oxygen atmosphere. Refluxing in concentric acids may be used as it is a known, effective method for the separation of the catalytic impurities. I. W. Chiang, B. E. Brinson, R. E. Smalley, J. L. Margrave, R. H. Hauge, *J. Phys. Chem. B,* 157 (2001) 1105-1161.

Hydrated ferric chloride and ferrous sulphate precursors were dissolved in 100 ml water and heated to 90° C., and then two solutions, 10 ml of ammonium hydroxide (25%) and 0.5 g of functionalized MWNTs dissolved in 50 ml of water, were added rapidly and sequentially. The mixture was stirred at 90° C. for 30 minutes and then cooled to room temperature. The black precipitate was collected by filtrating and washed to neutral with water. The obtained black precipitate was $Fe_3O_4$/MWNT nanoparticles and was ready for use.

Core-shell $Fe_3O_4@SiO_2$/MWNT nanoparticles were prepared by growing silica layers onto the surface of the $Fe_3O_4$/MWNTs according to known methods. Z. Lu, J. Dai, X. Song, G. Wang, W. Yang, *Colloids Surf A,* 317 (2008) 450-456. Twenty-five milliliters of ethanol, 1 ml water, 1 ml ammonium hydroxide and 150 µl of TEOS were added in a 250 ml three neck flask in a 40° C. water bath. $Fe_3O_4$/MWNTs were added to the above solution under mechanical stirring. Aliquots of the mixture were taken out after 12 h by centrifugation and washed with dI water and vacuum-dried at 50° C. overnight.

Example 1B

Fabrication of Biosensor

A schematic illustration of the fabrication of the biosensor is shown in FIG. 1 and further described below.

A glassy carbon electrode (GCE, 3-mm diameter) was first polished on chamois leather with 0.05 µm alumina slurry and then washed ultrasonically in doubly distilled water, anhydrous ethanol, and doubly distilled water, respectively. The cleaned GCE was allowed to dry at room temperature.

$Fe_3O_4@SiO_2$/MWNTs were sonicated in 0.5% Nafion solution to give a concentration of ~1 mg/ml. Four microliters of the $Fe_3O_4@SiO_2$/MWNTs suspension was film-cast onto the surface of the GCE and allowed to dry slowly. Films formed from Nafion-solubilized MWNTs were uniform and stable. Nafion also assists in the dispersion of $Fe_3O_4@SiO_2$/MWNTs and the Nafion-$Fe_3O_4@SiO_2$/MWNTs nanocomposite remains well dispersed on prolonged standing. Both the concentration of the $Fe_3O_4@SiO_2$/MWNTs in the Nafion solution and the volume of the solution used in film-casting may be adjusted to provide GCEs loaded with various amounts of $Fe_3O_4@SiO_2$/MWNTs.

16 µA of 100 U glucose oxidase (GOD) solution was film-cast onto the surface of the $Fe_3O_4@SiO_2$/MWNTs/GCE and allowed to dry slowly at 4° C. The obtained $Fe_3O_4@SiO_2$/MWNTs/GCE was washed carefully with DI water and dried at less than 4° C. The $Fe_3O_4@SiO_2$/MWNTs/GCE were coated with an extra 2.5 µl layer of 0.5% Nafion. Electrodes were rinsed with pH 7 phosphate buffer solution (PBS) and stored in the buffer at 4° C. prior to use.

Characterization of Nanocomposites and Nanocomposite-Based Biosensors

Methods

The electrochemical measurements were performed with CH Instruments CHI 608C Electrochemical Analyzer/Workstation. A platinum wire counter electrode, Ag/AgCI (3 M KCI) reference electrode and glassy carbon electrode (GCE, diameter 3 mm) were inserted into a modified 5-10 ml glass cell for the measurement. All potentials were referred to the Ag/AgCI reference electrode. Samples were characterized using different techniques. Powder X-ray diffraction (XRD) studies were carried out using a X'Pert PRO, PANalytical diffractometer with nickel-filtered Cu Kα radiation as the X-ray source. Samples were scanned in steps of 0.016° in the 2θ range 10-90°. Identification and characterization of functional groups were carried out using a PerkinElmer fourier transform infrared spectrometer (FT-IR) in the range 300-4000 $cm^{-1}$. The surface morphology of samples were done by using scanning tunneling microscope (SEM) (FEI; QUANTA scanning electron microscope) with an energy dispersive X-ray analysis (EDX) system. The EDX system attached with the SEM enables the elemental analysis of the samples. Transmission electron microscopy (TEM) images were obtained on a transmission electron microscope (TEM, JEOL JEM-2010F). UV absorption spectra of the samples in deionized water were recorded on JASCO Corp., V-570 spectrophotometer. Magnetic study of the samples had been done by vibrating sample magnetometer (VSM).

Example 2A

XRD and FT-IR studies of nanocomposites

Figure 2:
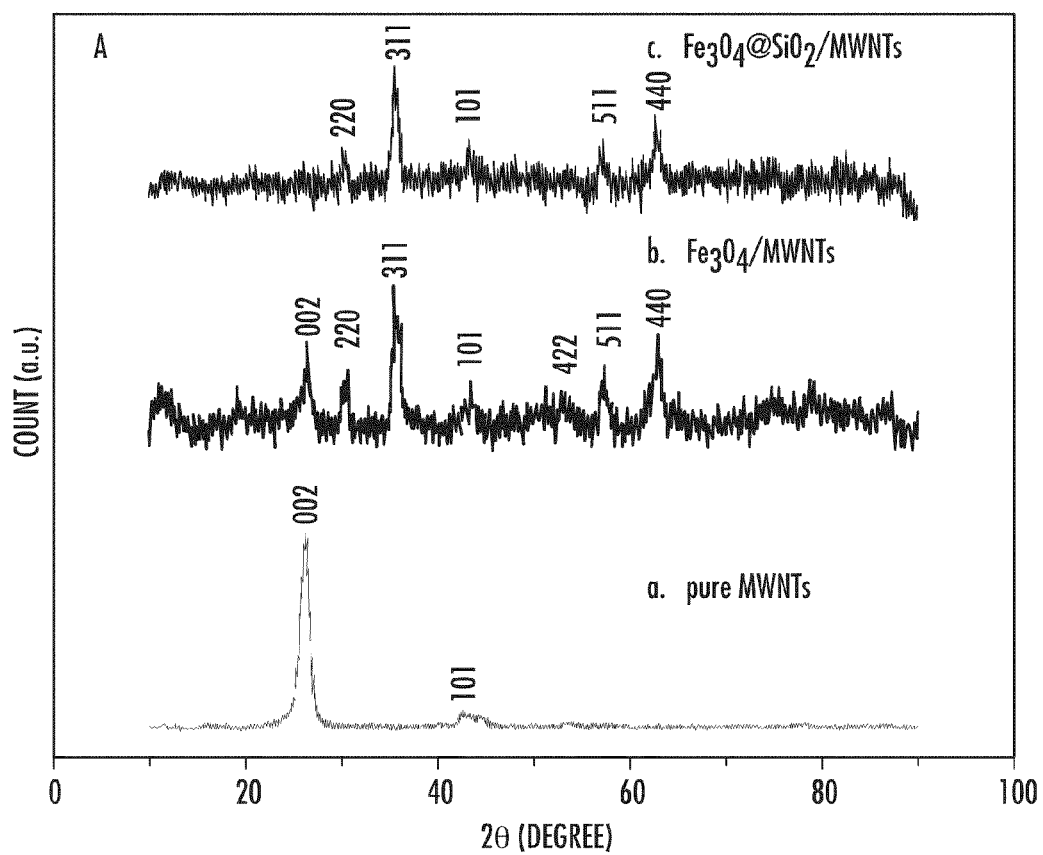
FIG. 2 are X-ray diffractograms of (a) pure MWNTs, (b) $Fe_3O_4$/MWNTs and (c) $Fe_3O_4@SiO_2$/MWNTs.

FIG. 2 shows the X-ray diffractogram of nanocomposites and a comparative MWNT sample. The XRD pattern indicates that the crystal structure of magnetic nanocomposites includes MWNTs, two phases of cubic $Fe_3O_4$/MWNTs and $Fe_3O_4@SiO_2$/MWNTs. Well-resolved diffraction peaks reveal the good crystallinity of the $Fe_3O_4$ specimens, which are located at 2θ of 30.28°, 35.56°, 43.3°, 53.68°, 57.36° and 62.72°, respectively. These data matched well with the data from Q. Lan, C. Liu, F. Yang, S. Y. Liu, J. Xu, D. J. Sun, J., *Colloid Interface Sci.,* 310 (2007) 260-269. The peaks in the $Fe_3O_4@SiO_2$/MWNTs reveal that even after the $SiO_2$ coating the sample retains its crystallinity. S. L. Tie, C. H. Lee, Y. S. Bae, M. B. Kim, K. Lee, C. H. Lee, *Colloid Surf. A,* 293 (2007) 278-285. The absence of $SiO_2$ peak in the XRD pattern in the nanocomposite is due to its amorphous structure coated on the $Fe_3O_4$ nanoparticles. The diffraction peak at 2θ=26.4° is the typical Bragg peak of pristine MWNTs and can be indexed to the (002) reflection of graphite. Judging from the pattern, the third phase does not exist. The average grain size (D) of the $Fe_3O_4$ particles was calculated using Scherrer's formula described by Equation 1, below.

$$D = \frac{0.9\lambda}{\beta\cos(\theta)} \quad \text{(Equation 1)}$$

In Equation 1, λ is wave length of X-ray used, β is FWHM of diffraction peak and θ is the angle corresponding to the peak. The calculated average grain sizes using 35.56° diffraction peak were about 25 nm. Moreover, the diffractive peaks of $Fe_3O_4$ are broadened, implying that the crystalline size of $Fe_3O_4$ particles is quite small.

Selectivity of the nanocomposite-based biosensors may be introduced by anchoring on the MWNTs surface, specific functional groups that selectively bind specific biomolecules. For example, carboxylic acid groups may be used to attach folic acid, or amine groups on biomolecules to the MWNTs. Also, ammonium-terminated triethyl glycol (functional group) may be used to attach mouse splenocyte (a bioactive molecule), or triethylene glycol coupled to a maleimido linker (functional group) may be used to attach peptides derived from VP1 protein of FMDV (a bioactive molecule).

Figure 3:
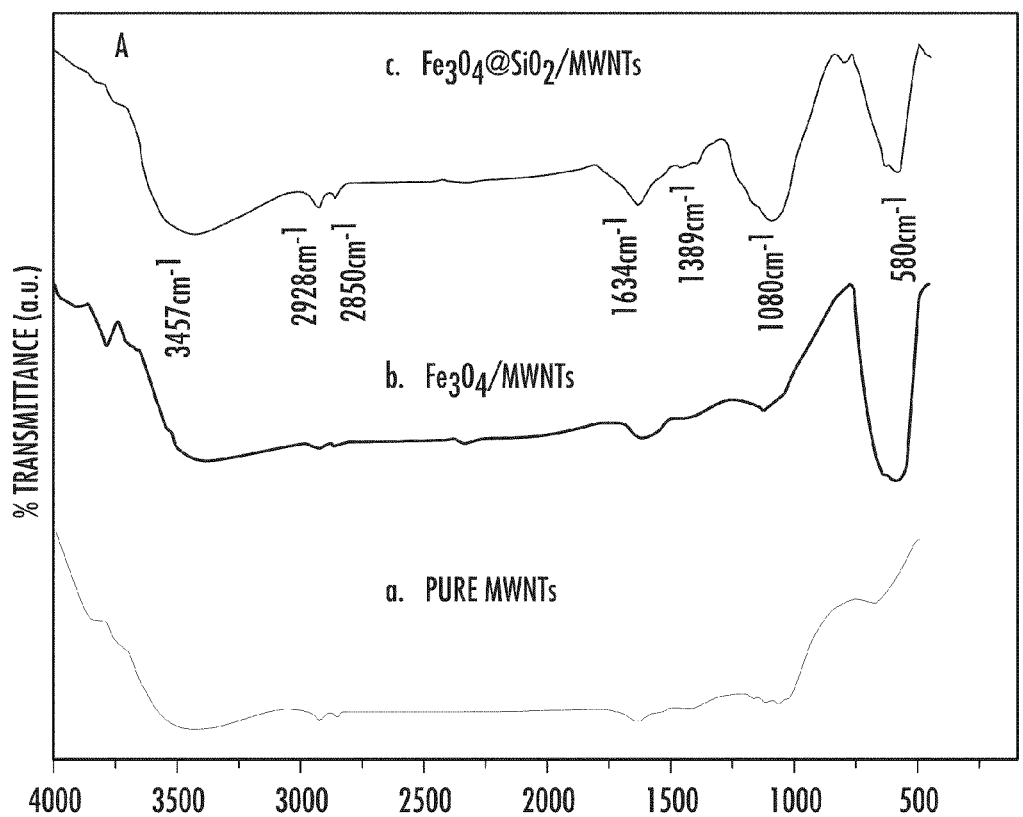
FIG. 3 includes FT-IR spectra of (a) pure MWNTs, (b) $Fe_3O_4$/MWNTs and (c) $Fe_3O_4@SiO_2$/MWNTs.

As shown in FIG. 3, all types of MWNTs showed peaks between 1300 and 1100 $cm^{-1}$, which are ascribed to the phenyl-carbonyl C—C stretch bonds. The peak between 3300-3500 $cm^{-1}$ is normally due to stretching vibration mode of OH and NH group. The peak at 3457 $cm^{-1}$ in curve (a) and curve (b) is due to OH group (due to oxidation with $HNO_3$) and in curve (c) it is due to both OH and —NH (from ammonia solution). There is a small broadening of this peak in the case of curve (c). As in curve (b), the peak at 568 $cm^{-1}$ is the stretching vibration due to the interactions of Fe—O—Fe in $Fe_3O_4$ and the peaks at 1383, 2850 and 2928 $cm^{-1}$ are attributed to the in-plane bending vibration of methyl (—$CH_3$) and the symmetric and asymmetric vibration of methylene (—$CH_2$—). Compared with the two spectra (b and c), the existence of the characteristic Si—O—Si peak at 1080 $cm^{-1}$ in curve (c) is direct evidence of the formation of the silica shell. In addition, comparing curves (b) and (c), the characteristic Fe—O—Fe peak of $Fe_3O_4$/MWNTs at 568 $cm^{-1}$ shifts to 580 $cm^{-1}$ in the spectrum of $SiO_2$ coated magnetic nanoparticles, providing further evidence that the silica shell is linked to the surface of the magnetic nanoparticles by a Fe—O—Si chemical bond. F. H. Chen, Q. Gao, J. Z. Ni, *Nanotechnology*, 19 (2008) 165103.

Example 2B

Magnetic and Optical Studies of Nanocomposites

Figure 4:
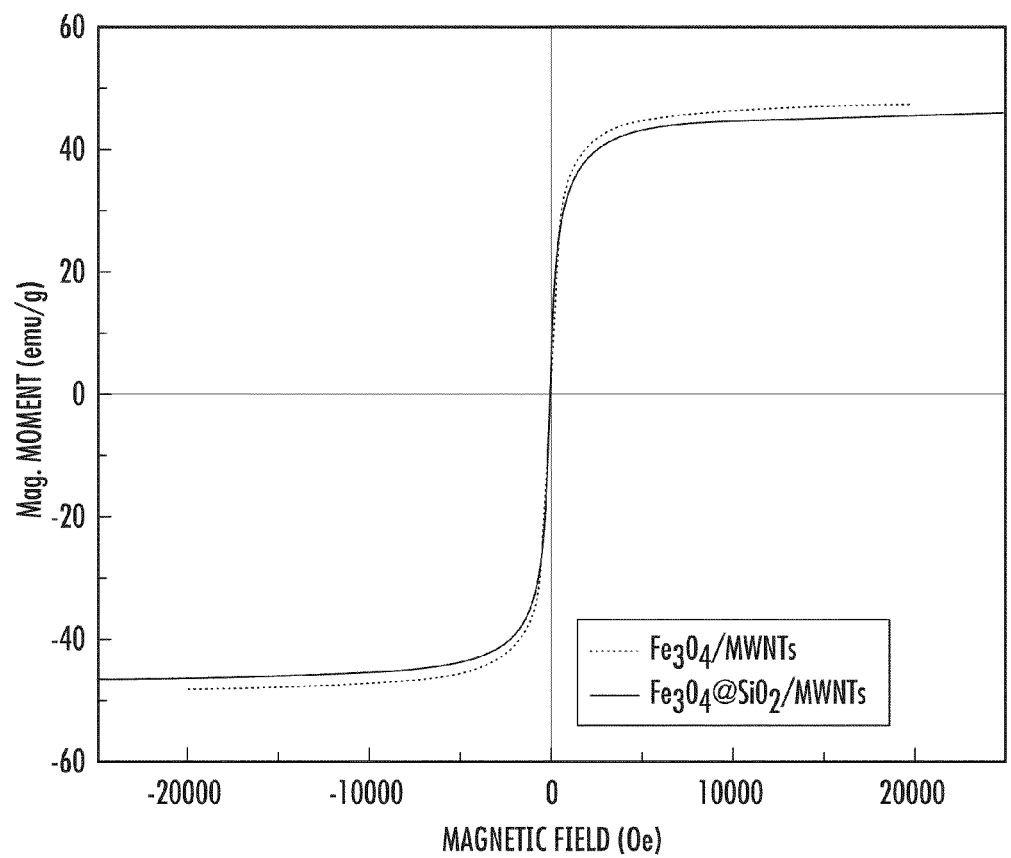
FIG. 4 shows a vibrating sample magnetometer (VSM) study of $Fe_3O_4$/MWNTs (red line) and $Fe_3O_4@SiO_2$/MWNTs (black line).

FIG. 4 shows the hysteresis loop of two nanocomposites at room temperature. The saturation magnetization of the $Fe_3O_4$@$SiO_2$/MWNT nanocomposite (~44 emu/g) is almost comparable to that of the $Fe_3O_4$/MWNT nanocomposite (~46 emu/g), indicating that the $Fe_3O_4$ nanoparticles covered by a silica network preserve their superparamagnetic properties.

Figure 5:
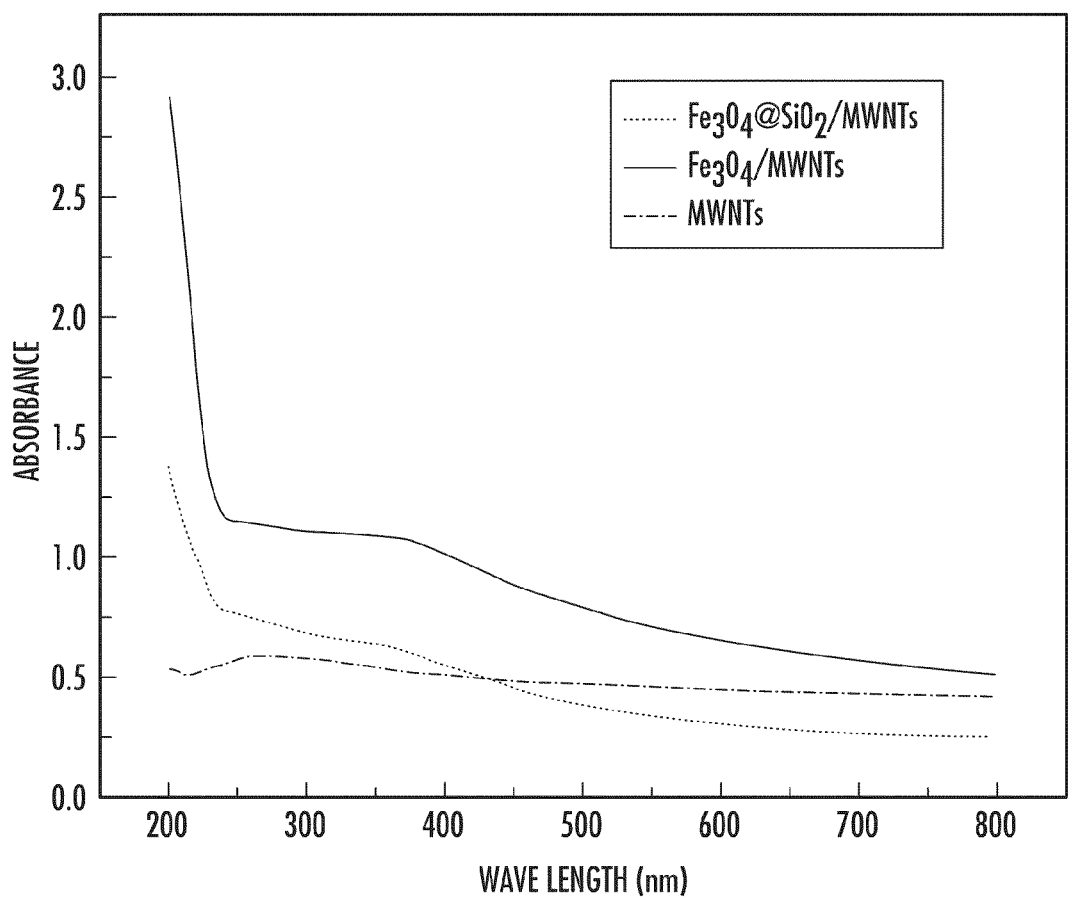
FIG. 5 shows UV-vis absorbance spectra of pure MWNTs (green), $Fe_3O_4$/MWNTs (black) and $Fe_3O_4@SiO_2$/MWNTs (red).
Figure 6A:
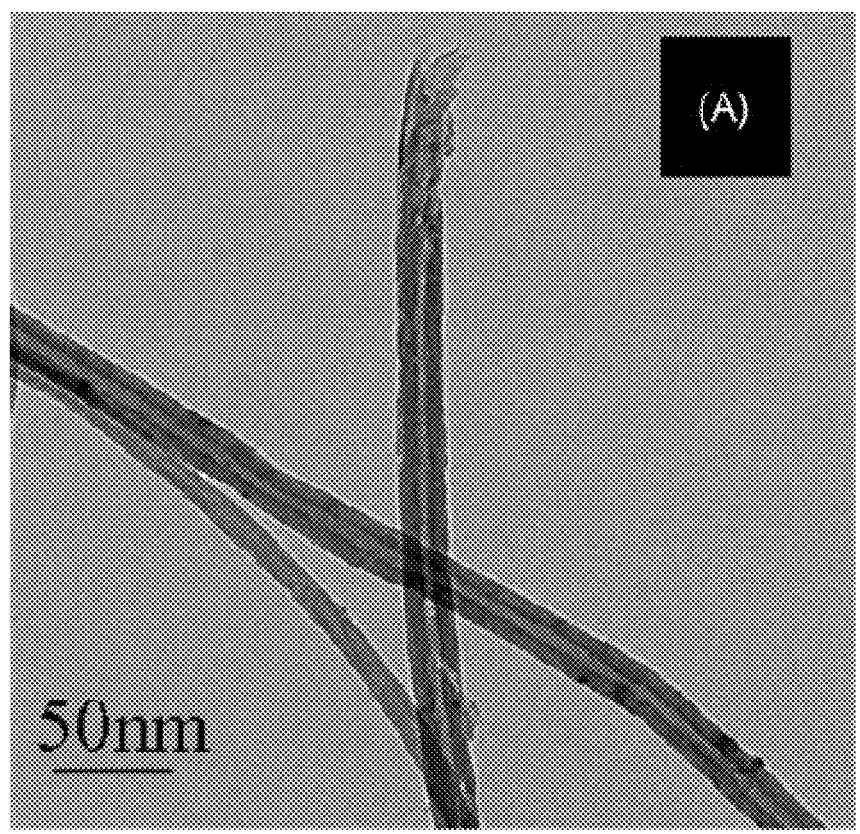
FIG. 6A is a TEM image of pure MWNTs.
Figure 6B:
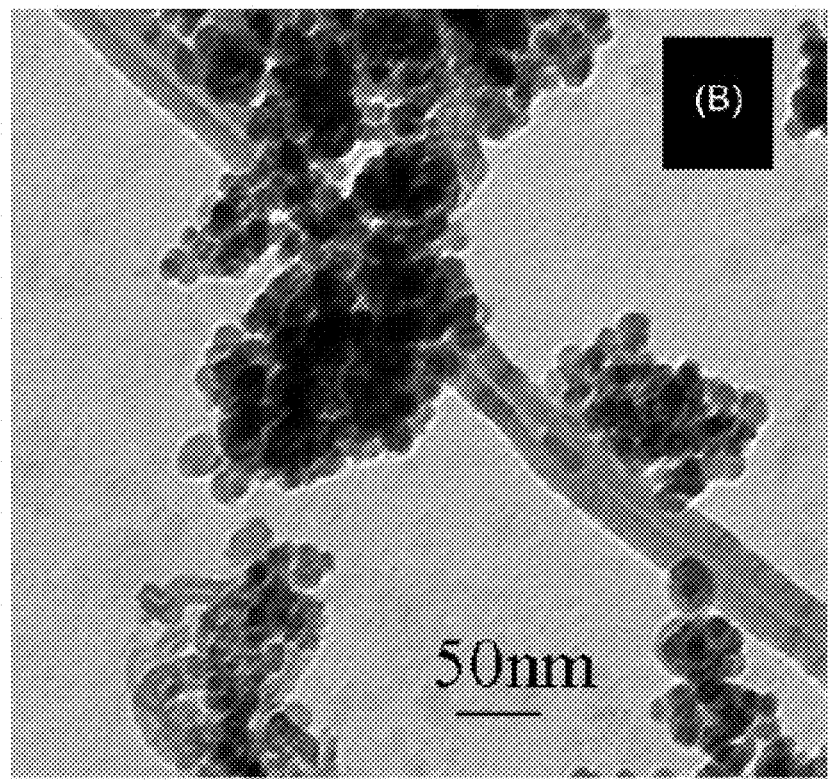
FIG. 6B is a TEM image of $Fe_3O_4@SiO_2$/MWNTs.
Figure 6C:
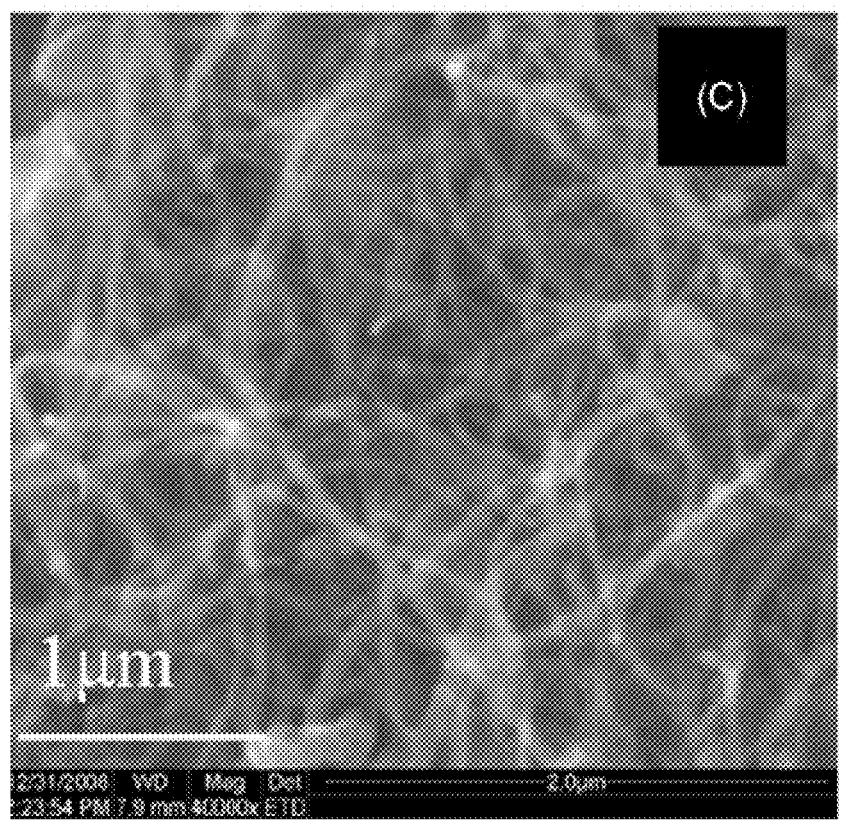
FIG. 6C is a SEM image of pure MWNTs.
Figure 6D:
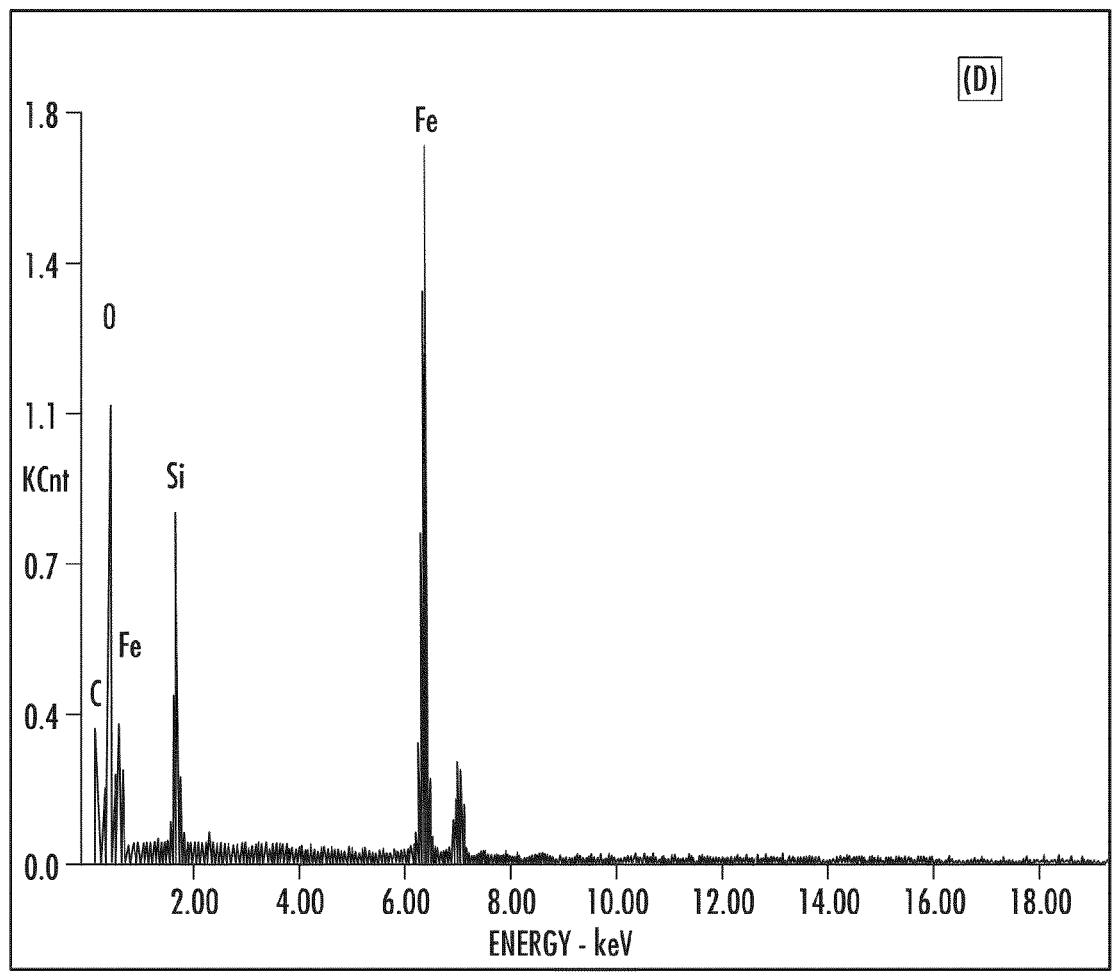
FIG. 6D is an energy dispersive X-ray analysis (EDX) for $Fe_3O_4@SiO_2$/MWNTs.

The UV-vis absorption spectra of different nanocomposites and comparative MWNT sample in deionized water are illustrated in FIG. 5. A very broad absorption peak appeared at about 267 nm, which originated from the C=C structure of MWNTs. C. S. Chen, X. H. Chen, B. Yi, T. G. Liu, W. H. Li, L. S. Xu, Z. Yang, H. Zhang, Y. G. Wang, *Acta Mater.*, 54 (2006) 5401-5407. The optical properties of all the magnetic nanoparticles used (with or without silica coating) are dominated by a broad featureless absorption tail characteristic of indirect band gap semiconductors. In the wavelength of >330 nm region, a broad featureless adsorption was observed in the curves with $SiO_2$ and without $SiO_2$, which originates primarily from the absorption and scattering of light by magnetic particles, in accordance with the literature. M. A. Correa-Duarte, M. Giersig, N. A. Kotov, L. M. Liz-Marzan, *Langmuir*, 14 (1998) 6430-6435. Again, this is characteristic of indirect band gap semiconductors. G. Dagan, W. M. Shen, M. Tomkiewicz, *J. Electrochem. Soc.*, 139 (1992) 1855-1861.

Example 2C

SEM and TEM Analysis of Nanocomposites

FIG. 6 shows SEM and TEM images of nanocomposites and a comparative MWNT sample. The morphology of the purified MWNTs was clearly visible from the SEM image shown in FIG. 6C. FIG. 6 also shows TEM images of the synthesized MWNTs (A) and the $Fe_3O_4$@$SiO_2$/MWNT nanocomposite (B). The open end of the MWNTs were clearly visible from the TEM image. The diameter of the MWNTs was about 25 nm. From the TEM and EDX shown in FIGS. 6B and 6D, respectively, it was determined that the magnetic nanoparticles were nearly in core-shell structures. The black color indicates the $Fe_3O_4$ core and the ash color indicates the $SiO_2$ shell, showing successful coating on the surface of the magnetic particles with silica. The EDX of FIG. 6D confirms the presence of iron and silicon in the sample. Inorganic compound functionalized iron oxide nanoparticles can greatly enhance the antioxidation properties for naked iron oxide nanoparticles.

Example 3

Figure 7A:
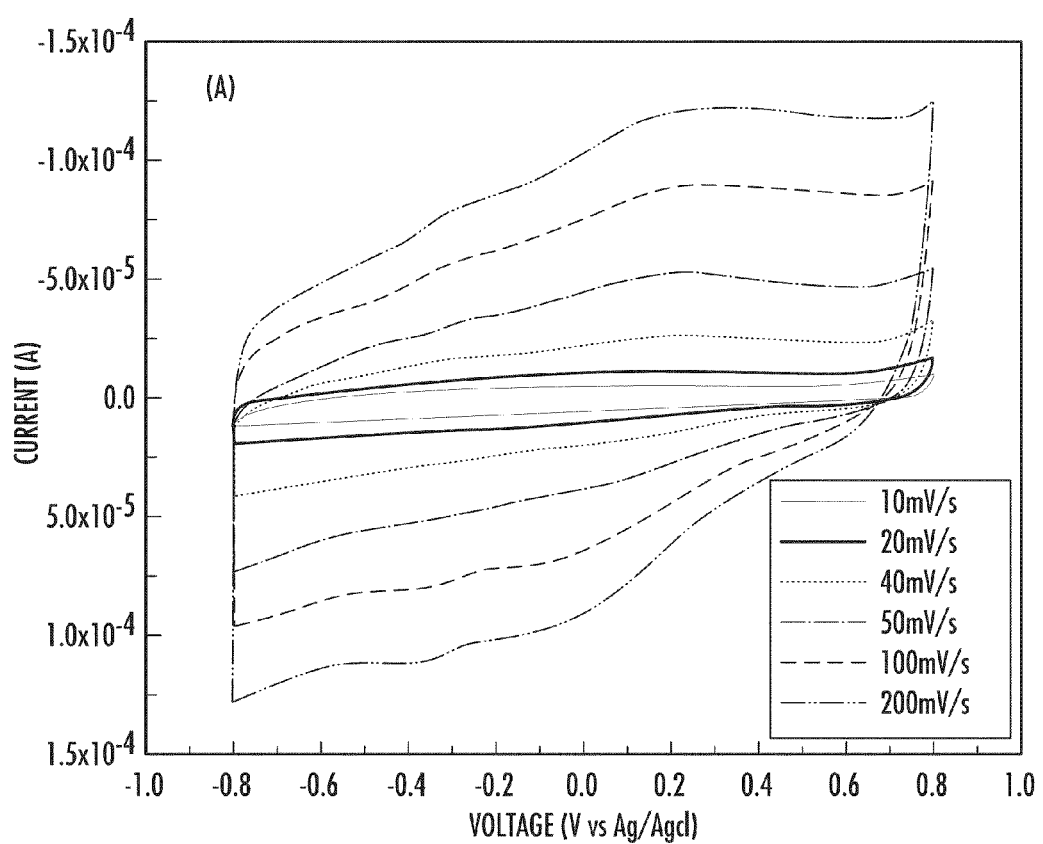
FIG. 7A shows cyclic voltammetry peak currents of the GOD/$Fe_3O_4@SiO_2$/MWNTs biosensor at different scan rates in PBS (0.1 M, pH 7).
Figure 7B:
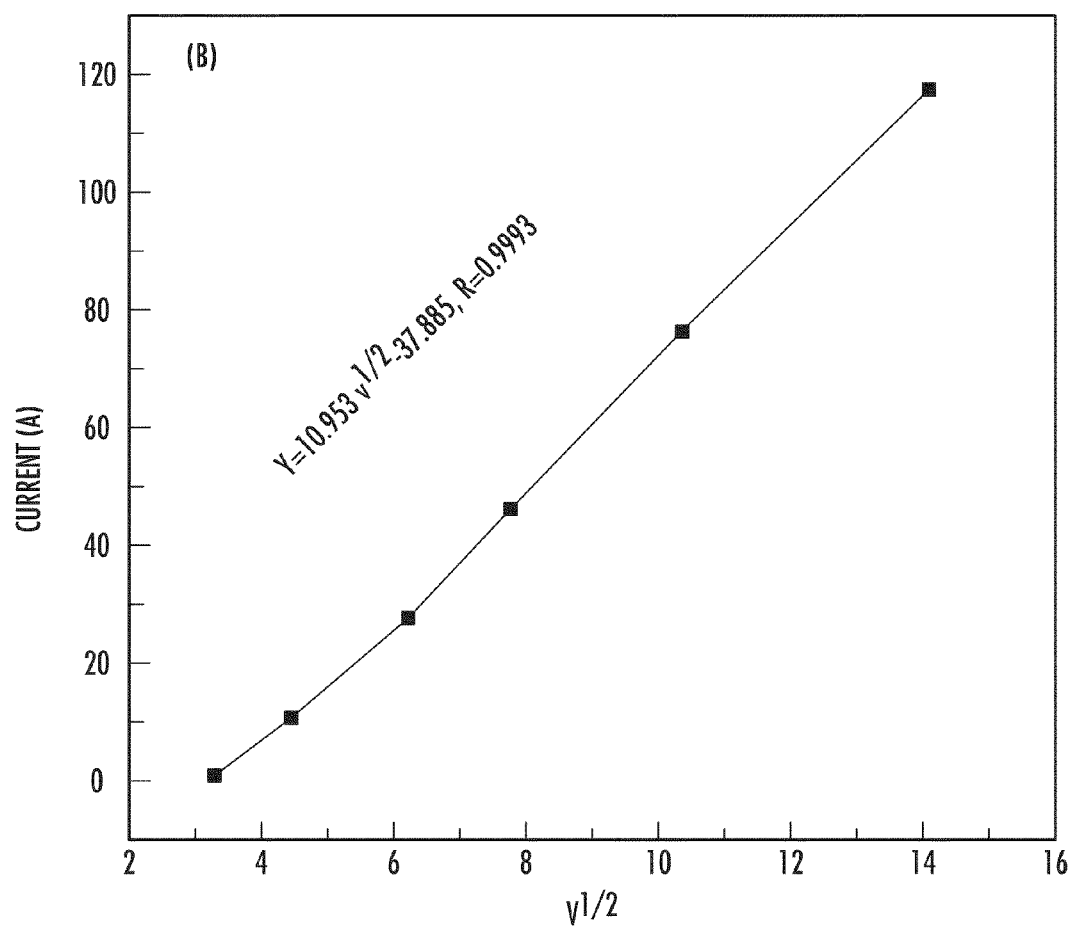
FIG. 7B shows the plot of peak anodic current vs. $v^{1/2}$ derived from the study of FIG. 7A.

Cyclic Voltammetry and Electrocatalytic Properties of Nanocomposite-Based Biosensors As shown in FIG. 7A, cyclic voltammetry peak currents of the GOD/$Fe_3O_4$@$SiO_2$/MWNTs biosensor increased with scan rate and the peak separation ($\Delta E_p$) was nearly independent of the scan rate. As shown in FIG. 7B, the anodic peak currents increased linearly with the increase of the square root of scan rate, suggesting that the electrochemical reaction is a diffusion-controlled process.

Figure 8A:
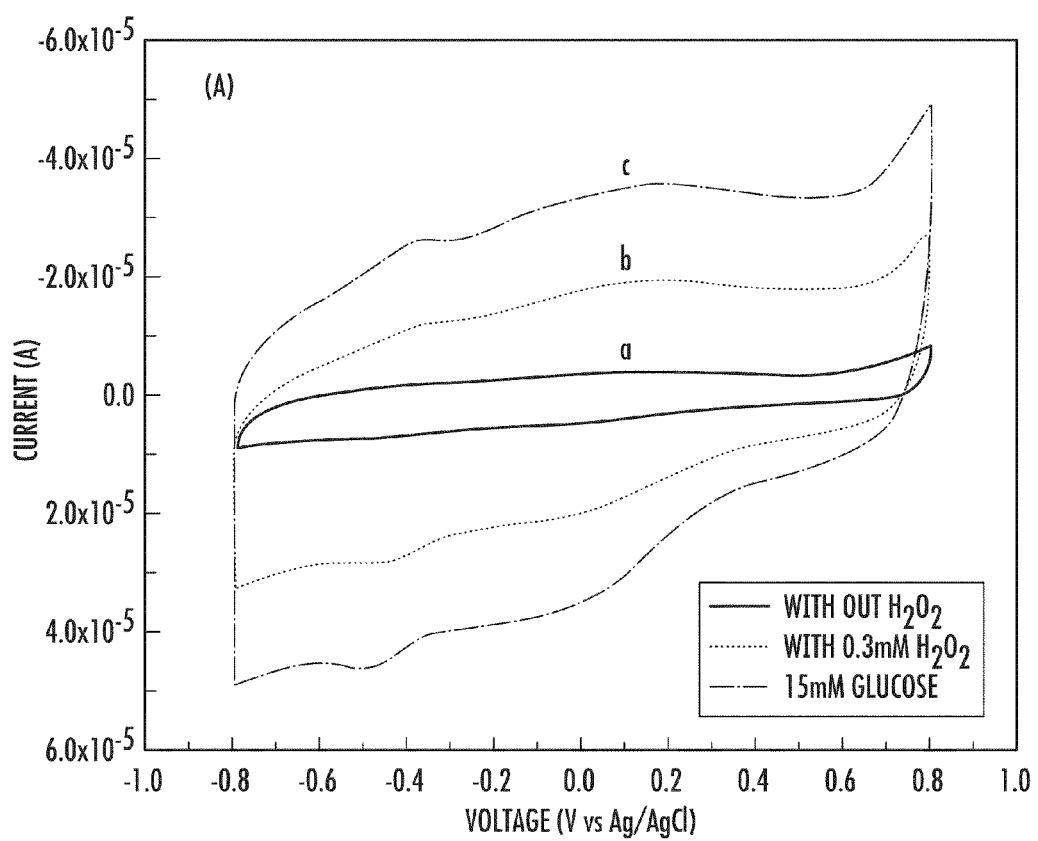
FIG. 8A shows the cyclic voltammetry (CV) peak currents of the GOD/$Fe_3O_4@SiO_2$/MWNTs biosensor (a) in PBS, (b) with 0.3 mM $H_2O_2$, and (c) with 15 mM glucose solution.

FIG. 8A shows the cyclic voltammograms of the GOD/$Fe_3O_4$@$SiO_2$/MWNTs biosensor in the absence (curve a), in the presence of 0.3 mM $H_2O_2$ (curve b) and in 15 mM glucose solution (curve c). The biosensor exhibits significant electrocatalysis to the oxidation and reduction of $H_2O_2$ starting around 0.1 V, which is even lower than that obtained with a conventional electrode using covalent binding immobilization (0.2V). C. E. Banks, R. G. Compton, *Analyst*, 130 (2005) 1232-1239. The superior performance of the fabricated GOD/$Fe_3O_4$@$SiO_2$/MWNTs biosensor toward the oxidation of $H_2O_2$ makes it extremely attractive for glucose sensing applications. In addition, when MWNTs were treated with the acid solution, the carboxylic acid functional groups introduced on the surface of the MWNTs, including at the ends of the nanotubes, were used to covalently bind glucose oxidase. Moreover, because the MWNTs have large surface area, it was possible to immobilize a large amount of glucose oxidase on the surface of the nanotubes, resulting in a high response current and expanding the detectable range of the biosensor for glucose.

Example 4

Effect of Electroactive Interferents on Nanocomposite-Based Biosensors

Figure 8B:
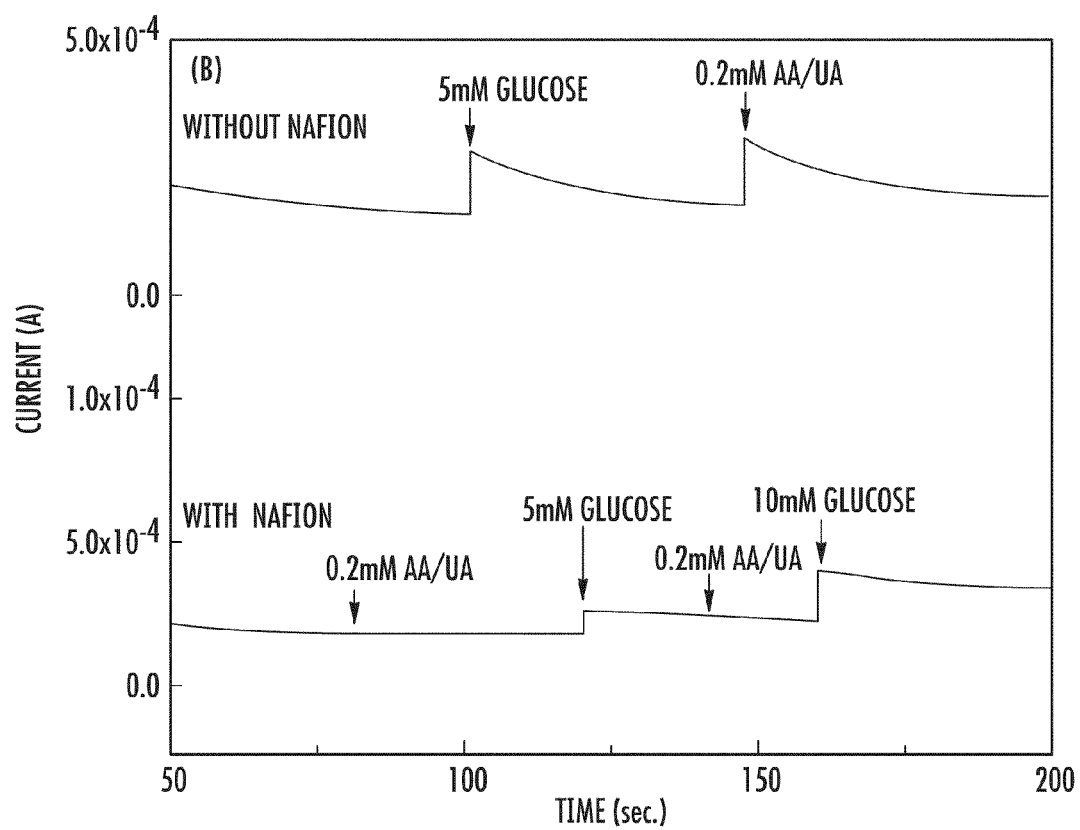
FIG. 8B shows the results of a study of interference from ascorbic acid and uric acid using a GOD/$Fe_3O_4@SiO_2$/MWNTs biosensor with and without an overlayer of Nafion.

The interference of some electroactive compounds to the glucose response was examined. A GOD/$Fe_3O_4$@$SiO_2$/MWNTs biosensor with a Nafion coating and a GOD/$Fe_3O_4$@$SiO_2$/MWNTs biosensor without a Nafion coating were added to a solution of 0.2 mM of ascorbic acid (AA) and uric acid (UA). The upper curve in FIG. 8B shows the results from the biosensor without Nafion and indicates the presence of AA and UA. The lower curve in FIG. 8B shows the interference study for the Nafion coated biosensor. For this biosensor, there was not much change in the current due to AA and UA, clearly showing that 25 µl of 0.5 wt % Nafion on the surface of the GOD/Fe$_3$O$_4$@SiO$_2$/MWNTs biosensor prevents the interference from AA and UA.

Example 5

Figure 9:
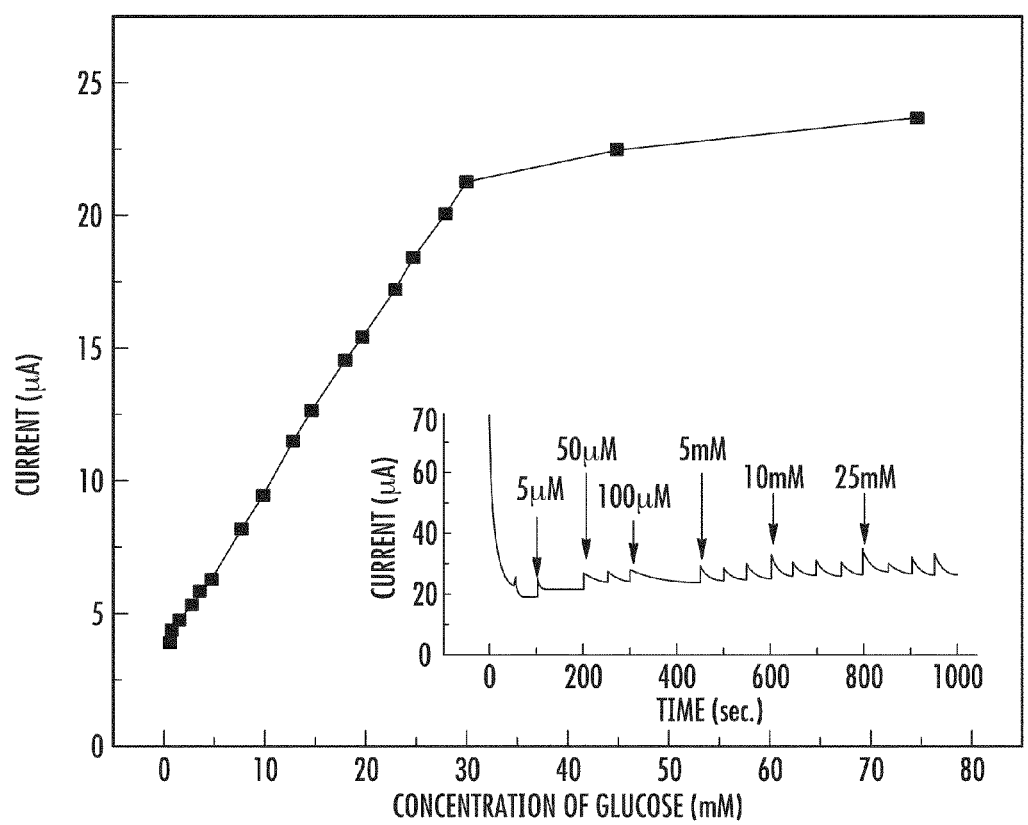
FIG. 9 shows the calibration curve of the a GOD/$Fe_3O_4@SiO_2$/MWNTs biosensor. The amperometric i-t curve obtained with the addition of different concentrations of glucose solution is shown in the inset.

Study of Amperometric i-t and Calibration Curve for Nanocomposite-Based Biosensors The amperometric responses of the GOD/Fe$_3$O$_4$@SiO$_2$/MWNTs biosensor for successive additions of different concentration of glucose are presented in FIG. 9 (inset). Well-defined current responses for glucose were obtained at the GOD/Fe$_3$O$_4$@SiO$_2$/MWNTs modified electrode. The reaction occurring at the biosensor is very fast in reaching a dynamic equilibrium upon each addition of the sample solution, generating a steady-state current signal within about 3 to 6 seconds. The calibration of the biosensor is depicted in FIG. 9. The steady-state currents gradually increased with increasing concentration of glucose, and exhibited a linear relationship with the concentration of glucose in the range from about 1 µM to about 30 mM with a detection limit of about 800 nM (estimated at S/N=3) with a correlation coefficient of 0.9994. The performance of the GOD/Fe$_3$O$_4$@SiO$_2$/MWNTs biosensor was surprisingly and unexpectedly superior than the reported value of a conventional biosensor using an electrode modified with Fe$_3$O$_4$@SiO$_2$ which is reported to exhibit a linear range of $1.0 \times 10^-$ to $4.0 \times 10^{-3}$ M with a detection limit of 3.2 µM. J. Qiu, H. Peng, R. Liang, *Electrochem. Commun.*, 9 (2007) 2734-2738.

From FIG. 9, it was also observed that the biosensor response gradually deviates from the linear feature as the glucose concentration reaches 30 mM. This is the characteristic of a Michaelis-Menten kinetics. The apparent Michaelis-Menten constant $K^{app}m$, which depicts the enzyme-substrate kinetics of biosensor, can be calculated from the Lineweaver-Burk equation, Equation 2, below.

$$\frac{1}{I_{ss}} = \left(\frac{K^{app}m}{I_{max}}\right)\left(\frac{1}{C}\right) + \frac{1}{I_{max}} \quad \text{(Equation 2)}$$

In Equation 2, C is the concentration of substrate, $I_{ss}$ the steady-state current and $I_{max}$ is the maximum current measured under substrate saturation. S. Zhang, W. Nü, H. Yu, Y. Niu, C. Sun, *Bioelectrochemistry*, 67 (2005) 15-22. Therefore the values of the $K^{app}m$ and $I_{max}$ in this can be calculated to be about 13 mM and about 25 µA, respectively. The lower $K^{app}m$ reflects the higher enzymatic activity of immobilized glucose oxidase, further indicating that the nanocomposite-based biosensor possesses a high affinity to glucose. X. Chu, D. Duan, G. Shen, R. Yu, *Talanta*, 71 (2007) 2040-2047.

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art, all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 particles refers to groups having 1, 2, or 3 particles. Similarly, a group having 1-5 particles refers to groups having 1, 2, 3, 4, or 5 particles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

All references cited herein are incorporated by reference in their entireties and for all purposes to the same extent as if each individual publication, patent, or patent application was specifically and individually incorporated by reference in its entirety for all purposes.

What is claimed is:

1. A biosensor comprising:
   an electrode having a surface;
   a nanocomposite on the surface of the electrode, the nanocomposite comprising magnetic nanoparticles dispersed on an outer surface of each member of a population of carbon nanotubes,
      wherein the magnetic nanoparticles comprise core-shell magnetic nanoparticles comprising a core comprising a ferromagnetic metal or compound thereof, and a shell comprising silicon dioxide; and
   one or more biomolecules over the surface of the electrode, wherein the biomolecules are configured to undergo a redox reaction with a target molecule;
   wherein the outer surface of the carbon nanotubes comprise one or more functional groups covalently bonded to the outer surface.

2. The biosensor of claim 1, wherein the magnetic nanoparticles comprise iron, nickel, cobalt, or a compound of iron, nickel, or cobalt.

3. The biosensor of claim 1, wherein the magnetic nanoparticles comprise nickel or cobalt, or a compound of nickel or cobalt.

4. The biosensor of claim 1, wherein the magnetic nanoparticles comprise cobalt, cobalt oxide, nickel, nickel oxide, or cobalt-iron oxide.

5. The biosensor of claim 1, wherein the magnetic nanoparticles comprise iron or a compound thereof.

6. The biosensor of claim 1, wherein the magnetic nanoparticles comprise iron oxide.

7. The biosensor of claim 1, wherein the magnetic nanoparticles comprise $Fe_3O_4$, cobalt, cobalt oxide, nickel, nickel oxide, or cobalt-iron oxide.

8. The biosensor of claim 1, wherein the carbon nanotubes comprise multiwalled carbon nanotubes.

9. The biosensor of claim 1, wherein the carbon nanotubes have an average outer diameter of about 30 nm to about 50 nm.

10. The biosensor of claim 1, wherein the functional groups comprise COOH, OH, NH, $NH_2$, F, COX, or SH, wherein X is F, Cl, Br, or I.

11. The biosensor of claim 1, wherein the biomolecules comprise cholesterol oxidase, DNA, or a cancer drug.

12. The biosensor of claim 1, wherein the biomolecules comprise glucose oxidase and the target molecule comprises glucose.

13. The biosensor of claim 12, wherein the biosensor exhibits a detection limit for glucose of about 800 nM or less.

14. The biosensor of claim 12, wherein the biosensor exhibits a linear response for glucose from about 1 µM to about 30 mM.

15. The biosensor of claim 1, wherein the magnetic nanoparticles comprise core-shell magnetic nanoparticles and the core comprises $Fe_3O_4$, further wherein the carbon nanotubes comprise multiwalled carbon nanotubes, and further wherein the biomolecules comprise glucose oxidase and the target molecule comprises glucose.

16. A nanocomposite comprising:
  a population of carbon nanotubes; and
  a population of magnetic nanoparticles dispersed on the outer surface of each member of the population of carbon nanotubes;
wherein:
  the magnetic nanoparticles comprise core-shell magnetic nanoparticles; and
  the core comprises a ferromagnetic metal or a compound thereof;
wherein the outer surface of the carbon nanotubes comprise one or more functional groups covalently bonded to the outer surface, wherein the one or more functional groups are selected from the group consisting of COOH, OH, NH, $NH_2$, F, COX, or SH, wherein X is F, Cl, Br, or I.

17. The nanocomposite of claim 16, wherein the shell comprises silicon dioxide.

18. The nanocomposite of claim 16, wherein the magnetic nanoparticles comprise iron, nickel, or cobalt.

19. A method for determining a concentration of a target molecule in a sample, the method comprising:
  exposing the sample to a biosensor, the biosensor comprising an electrode;
  a nanocomposite on the surface of the electrode, the nanocomposite comprising magnetic nanoparticles dispersed on an outer surface of each member of a population of carbon nanotubes,
  wherein the magnetic nanoparticles comprise core-shell magnetic nanoparticles comprising a core comprising a ferromagnetic metal or compound thereof, and a shell comprising silicon dioxide; and
  one or more biomolecules over the surface of the electrode, wherein the biomolecules are configured to undergo a redox reaction with a target molecule, wherein the outer surface of the carbon nanotubes comprise one or more functional groups covalently bonded to the outer surface, and
  detecting a signal from the biosensor, wherein the signal is correlated to the concentration of the target molecule in the sample.

* * * * *

UNITED STATES PATENT AND TRADEMARK OFFICE
CERTIFICATE OF CORRECTION

PATENT NO. : 8,956,517 B2
APPLICATION NO. : 12/827613
DATED : February 17, 2015
INVENTOR(S) : Sundara et al.

It is certified that error appears in the above-identified patent and that said Letters Patent is hereby corrected as shown below:

On the Title Page, item (56), under "OTHER PUBLICATIONS", in Column 1, Line 13, delete "Electocatalytic" and insert -- eletrocatalytic --, therefor.

On the Title Page, item (56), under "OTHER PUBLICATIONS", in Column 2, Line 2, delete "nanotube/nano-Fe3O4" and insert -- nanotube/nano-$Fe_3O_4$ --, therefor.

On Title Page 2, item (56), under "OTHER PUBLICATIONS", in Column 2, Line 21, delete "Fe3O4@SiO2" and insert -- $Fe_3O_4@SiO_2$ --, therefor.

On Title Page 2, item (56), under "OTHER PUBLICATIONS", in Column 2, Line 26, delete "SiO2" and insert -- $SiO_2$ --, therefor.

On Title Page 2, item (56), under "OTHER PUBLICATIONS", in Column 2, Line 32, delete "Fe3O4" and insert -- $Fe_3O_4$ --, therefor.

In the Specification

In Column 4, Line 1, delete "the a" and insert -- the --, therefor.

In Column 5, Line 27, delete "Superparamagetism" and insert -- Superparamagnetism --, therefor.

In Column 9, Line 32, delete "Surf" and insert -- Surf. --, therefor.

In Column 9, Line 64, delete "µA" and insert -- µl --, therefor.

In Column 10, Line 58, delete "below." and insert -- below: --, therefor.

In Column 13, Line 31, delete "$1.0\times10^{-5}$" and insert -- $1.0\times10^{-5}$ --, therefor.

In Column 13, Line 40, delete "below." and insert -- below: --, therefor.

Signed and Sealed this
Eleventh Day of August, 2015

Michelle K. Lee
*Director of the United States Patent and Trademark Office*